United States Patent [19]

Krumkalns

[11] 4,338,118

[45] Jul. 6, 1982

[54] PLANT GROWTH REGULATION

[75] Inventor: Eriks V. Krumkalns, Indianapolis, Ind.

[73] Assignee: Eli Lilly and Company, Indianapolis, Ind.

[21] Appl. No.: 276,588

[22] Filed: Jun. 23, 1981

[51] Int. Cl.$^3$ .............................................. A01N 43/40
[52] U.S. Cl. ............................................ 71/76; 71/94
[58] Field of Search ........................................ 71/94, 76

[56] References Cited

U.S. PATENT DOCUMENTS 3,905,798  9/1975  Zeeh, et al. ............................ 71/76

OTHER PUBLICATIONS

Technical Data Sheet and Specimen Label for PIX, BASF Wyandotte Carp., May. 1978.
Lavagnino et al., JACS 82, 2609 (1960).
Jung, "Plant Regulation and World Agriculture", Chapter 16, pp. 279–307 (Plenum Press, N.Y. 1980).

*Primary Examiner*—Catherine L. Mills
*Attorney, Agent, or Firm*—Charles W. Ashbrook; Arthur R. Whale

[57] ABSTRACT

Bicyclic quaternary ammonium salts are useful in a method of plant growth regulation.

9 Claims, No Drawings

PLANT GROWTH REGULATION

BACKGROUND OF THE INVENTION

U.S. Pat. No. 3,905,798 discloses several nitrogen containing monocyclic compounds in the form of quaternary ammonium salts which are useful as plant growth regulators. Of particular interest among such compounds is N,N-dimethylpiperidinium chloride. This compound has demonstrated excellent growth regulator activity on cotton. In discussing this and similar compounds, Jung, in Chapter 16 of "Plant Regulation and World Agriculture" 279–307 (1980, Plenum Press, New York), notes that very slight structural modifications to such compounds can totally destroy the growth regulator activity. Indeed, Jung points out that of a very large number of quaternary ammonium compounds evaluated, several demonstrated a complete lack of activity.

Since the structure-activity relationship among quaternary ammonium salts of the type described above is known to be quite specific and narrow, it is surprising to find that compounds differing rather substantially in structure display comparable growth regulator activity. It has now been discovered that a group of nitrogen containing bicyclic quaternary ammonium salts demonstrate excellent plant growth regulator activity.

Among the compounds which are the subject of this invention are a group of conidinium quaternary salts. Conidine is the name given to a 4,6-bicyclic ring system containing a single bridgehead nitrogen atom. Conidinium quaternary salts were first prepared by Loffler et al. in 1907, Ber., 40, 1310 (1907), and later by Lavagnino et al., J. Am. Chem. Soc., 82, 2609 (1960). Lavagnino et al. additionally describes the preparation of octahydropyrrocoline, the quaternary ammonium salts of which are also useful in the method of this invention.

Quinuclidine is similar to conidine in that it is a nitrogen containing bicyclic ring system. It differs structurally in being a 6,6-bicyclic system rather than a 4,6-system. Like the conidine series, quinuclidine and quaternary ammonium salts of quinuclidine are well known in the art.

The use of bicyclic quaternary ammonium salts such as quinuclidine salts and conidinium salts as plant growth regulators is heretofore unknown. This invention provides a method of controlling vegetative growth employing these bicyclic compounds.

SUMMARY OF THE INVENTION

This invention concerns plant growth regulation employing known compounds. More particularly, this invention provides a method for controlling vegetative growth of plants comprising applying to the plants or to the locus where plants are growing a growth regulating amount of a quaternary ammonium salt of the formula

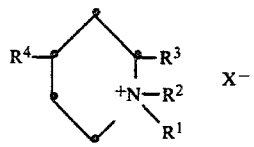

wherein:
$R^1$ is methyl or ethyl;
$R^2$, taken together with either $R^3$ or $R^4$, is —CH$_2$CH$_2$— or —CH$_2$CH$_2$CH$_2$—;
$R^3$ and $R^4$ independently are hydrogen, or separately taken together with $R^2$, are —CH$_2$—CH$_2$— or —CH$_2$CH$_2$CH$_2$—; provided that one and only one of $R^3$ and $R^4$ is hydrogen;
$X^-$ is chloride, bromide or iodide.

DETAILED DESCRIPTION OF THE INVENTION

All of the compounds to be employed in the method of plant growth regulation provided by the present invention are known in the art. The compounds are prepared by reaction of methyl or ethyl chloride, bromide or iodide with a bicyclic amine such as octahydropyrrocoline, conidine or quinuclidine. For example, reaction of conidine with about an equimolar amount or an excess of methyl chloride affords methyl conidinium chloride.

The quaternization of the bicyclic amines generally is carried out in an unreactive organic solvent such as methylene chloride, diethyl ether or acetone, and typically at a temperature of about 0° to about 50° C. The salts form within about 10 to about 90 minutes, and can readily be isolated by removing the reaction solvent followed by crystallization of the product from solvents such as ethanol or acetone.

Exemplary of the compounds to be employed in the method of this invention are:
methyl conidinium bromide;
methyl conidinium iodide;
ethyl conidinium chloride;
ethyl conidinium bromide;
methyl quinuclidinium bromide;
methyl quinuclidinium iodide;
ethyl quinuclidinium chloride;
methyl octahydropyrrocolinium bromide;
ethyl octahydropyrrocolinium iodide;
methyl-1-azoniabicyclo[3,2,2]nonane bromide; and
ethyl-1-azoniabicyclo[3,2,2]nonane chloride.

The method of this invention is preferably carried out employing a compound of the above formula wherein $R^1$ is methyl. The method is especially preferred when employing a methyl conidinium salt such as methyl conidinium chloride.

The method of regulating the growth pattern of plants according to this invention is practiced in the usual manner of plant growth regulation. Typical plant responses which are embraced by terms such as "plant growth regulation" include inhibition of vegetative growth in woody and herbaceous plants, control of flowering, inhibition of seed formation, control of fruiting, delay in maturation, and related growth regulatory responses.

The growth regulatory action of the compounds defined above may be advantageously employed in various ways. The production of shorter and thicker stems in cereal grains such as wheat, barley and oats may reduce the tendency toward lodging and thus result in reduced economic loss due to adverse weather conditions. Turf grasses may be maintained at a desirably low height and the necessity for frequent mowing alleviated. The plant growth on embankments, such as roadsides, may be controlled to prevent erosion and at the same time maintain its aesthetic value with a minimum of maintenance. The control of flowering and fruiting may be advantageous in the production of seedless fruit and for hybridization. Modifying the vegetative process or altering the time of flowering and fruiting may result in more advantageous harvest dates or increased or modified flower, fruit or seed production. A preferred aspect of this invention permits the growth regulation of cotton so that total plant height as well as lateral branch length is reduced, thereby providing a more compact plant which in turn facilitates harvesting and improves yield. Other applications employing compounds defined herein will suggest themselves to those skilled in the art of agriculture and plant growth regulation.

The various plant species whose growth can be regulated according to the method of the invention includes cucumber, bluegrass and related turf species, bean species such as soybean, the various green snapbean varieties, crop species such as corn, wheat, rape, rye, flax, rice, cotton, sugarcane, as well as fruit species such as tomato, potato and the like. Various species of flowers such as chrysanthemum and the like also can be treated according to the method of this invention.

The method for regulating the growth of plants provided by this invention comprises applying to the plants an effective amount of a plant growth regulator as defined by the above general formula. The application of active compounds can be accomplished by contacting the foliage of the plants with the active compound, or if desired simply applying the compound to the habitat in which the plant whose growth is to be regulated is growing.

The specific amount of active growth regulator compound to be applied according to the new method will of course be determined by one or more of several factors, including the particular plant species being treated, the mode of application, the soil texture and moisture content, the particular time during the growing cycle the method is practiced, and related factors. Generally, the bicyclic quaternary salts will be applied at an effective rate of about 0.01 to about 20 pounds per acre, more preferably at an effective rate of about 0.5 to about 1.5 pounds per acre.

For use as contemplated according to the method of this invention, the bicyclic quaternary salt growth regulator compounds are formulated into compositions suited to soil, surface, or foliar application to plants and areas where plants are growing. The compounds can be formulated with any number of well known and routinely used agronomically-acceptable carriers, diluents, excipients and the like. The compositions may take the form of wettable powders, dusts, granules, solutions, emulsifiable concentrates, emulsions, suspension concentrates and the like. Such compositions generally contain from about 1 to about 95 percent by weight active ingredient.

A preferred composition for use according to the present method is a wettable powder. Wettable powders generally contain from about 20 to about 80 percent by weight of active ingredient. The remainder of the composition consists of solid carriers and wetting agents. Commonly utilized solid carriers include bentonite, fuller's earth, diatomaceous earth, diatomaceous silica, talc, chalk, hydrated silica, expanded mica, and related carriers. Wetting agents and surfactants commonly employed include condensed aryl sulfonic acids, sodium lignosulfate, sulfonateoxide condensate blends, alkyl aryl polyether alcohols, anionic and nonionic wetting agents, and the like.

Another commonly used composition form is a dust. Dusts generally contain about 5 to about 10 percent by weight of active ingredient admixed with a solid carrier such as clay or fuller's earth or the like.

Granules represent another important form of composition to be employed in the present method. Granules generally contain about 1 to about 30 percent by weight of active ingredient, admixed with a solid carrier such as silica or clay. Slow release modifiers such as polymers can be employed if desired. Also, binding agents such as sugar derivatives and polyvinylpyrrolidones can be incorporated into such compositions.

The compounds employed in the method of this invention can be used individually or in a mixture with one or more other active compounds. For example, the bicyclic quaternary salts defined herein can be used in combination with other plant growth regulators such as the polymeric N-vinyl-2-oxazolidinones, N-dimethylamino-1,2,3,6-tetrahydrophthalamic acid and its salts, pyridones, mefluidide and its related compounds as described in U.S. Pat. No. 3,894,078, the monocyclic quaternary salts described in U.S. Pat. No. 3,905,798, and other commonly used plant growth regulators. The bicyclic quaternary compounds can also be employed in combination with other commonly used agricultural chemicals such as herbicides, fungicides, insecticides and plant bactericides.

The plant growth regulator activity of the compounds defined above has been demonstrated for several representative compounds both in standard greenhouse studies and in open field studies. In a typical greenhouse plant growth regulator screen, the compounds were evaluated in replicated tests on cotton. The compounds to be evaluated were formulated by dissolving 20 mg. of test compound in 30 ml. of a solution containing 3 ml. of a 1:1 v/v solution of ethanol and acetone and 27 ml. of deionized water containing 300 ppm Toximul R and 400 ppm Toximul S surfactants. The formulated compounds were evaluated as a soil drench and as a foliar spray. The formulation was diluted with water and applied to the soil in which the various plant species were growing. Foliar spray applications were made with a DeVilbiss atomizer.

Evaluations of plant growth regulator activity were made by measuring the reduction in plant height caused by a test compound. Results of such a test on cotton is presented in the following Table.

TABLE 1

| Compound Tested | Concentration ppm | Percent Height Reduction | |
|---|---|---|---|
| | | 25 days post application | 32 days post application |
| Control | — | 0 | 0 |
| N-methyl-conidinium chloride | 50 | 29 | 31 |
| | 100 | 33 | 34 |
| | 200 | 41 | 41 |
| N-methyl-conidinium iodide | 50 | 14 | 13 |
| | 100 | 30 | 29 |
| | 200 | 42 | 39 |
| N-ethyl-conidinium iodide | 50 | 3 | 12 |
| | 100 | 0 | 0 |
| | 200 | 6 | 7 |
| N-methyl-quinuclidinium chloride | 50 | 17 | 17 |
| | 100 | 15 | 17 |
| | 200 | 30 | 29 |
| N-methyl-quinuclidinium iodide | 50 | 17 | 17 |
| | 100 | 21 | 22 |
| | 200 | 34 | 25 |
| N-ethyl-quinuclidinium iodide | 50 | 0 | 0 |
| | 100 | 5 | 4 |
| | 200 | 8 | 9 |

As noted above, the method of this invention is ideally suited for controlling vegetative growth of cotton. Practice of the method on cotton can result in an increase in yield of the first picking, and generally an increase in total yield. The compounds are effective in reducing total plant height as well as lateral branch length thus providing for a more compact cotton plant.

The method can advantageously be practiced on cotton by applying an effective amount of a compound defined herein to cotton plants at an early bloom stage, for example, when the cotton is from about 16 to about 30 inches tall. Subsequent applications can be made if needed to control growth.

I claim:

1. A method for reducing the height and lateral braching of a cotton plant comprising applying to a plant or to the locus where a plant is growing an effective amount of a compound of the formula

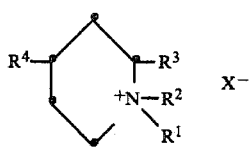

wherein:

$R^1$ is methyl or ethyl;

$R^2$, taken together with either $R^3$ or $R^4$, is —CH$_2$CH$_2$— or —CH$_2$CH$_2$CH$_2$—;

$R^3$ and $R^4$ independently are hydrogen, or separately taken together with $R^2$ are —CH$_2$CH$_2$— or —CH$_2$CH$_2$CH$_2$—;

provided that one and only one of $R^3$ and $R^4$ is hydrogen;

$X^-$ is chloride, bromide or iodide.

2. The method of claim 1 employing a compound wherein $R^1$ is methyl.

3. The method of claim 2 employing a compound wherein X is chloride.

4. The method of claim 2 employing a compound wherein X is iodide.

5. The method of claim 2 employing a compound wherein $R^2$ and $R^3$ together are —CH$_2$CH$_2$— and $R^4$ is hydrogen.

6. The method of claim 5 employing a compound wherein X is chloride.

7. The method of claim 5 employing a compound wherein X is iodide.

8. The method of claim 2 employing a compound wherein $R^2$ and $R^4$ together are —CH$_2$CH$_2$— and $R^3$ is hydrogen.

9. The method of claim 8 employing a compound wherein X is chloride.

* * * * *